United States Patent
Elsheikh et al.

(10) Patent No.: US 9,725,384 B2
(45) Date of Patent: Aug. 8, 2017

(54) METHOD FOR SEPARATING ORGANOFLUORINE COMPOUNDS USING MEMBRANE

(71) Applicant: Arkema Inc., King of Prussia, PA (US)

(72) Inventors: Maher Y. Elsheikh, Wayne, PA (US); John A. Wismer, Washington Crossing, PA (US); Sri R. Seshadri, Holland, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/903,627

(22) PCT Filed: Jul. 8, 2014

(86) PCT No.: PCT/US2014/045644
§ 371 (c)(1),
(2) Date: Jan. 8, 2016

(87) PCT Pub. No.: WO2015/006258
PCT Pub. Date: Jan. 15, 2015

(65) Prior Publication Data
US 2016/0152536 A1    Jun. 2, 2016

Related U.S. Application Data

(60) Provisional application No. 61/845,405, filed on Jul. 12, 2013, provisional application No. 61/989,031, filed on May 6, 2014.

(51) Int. Cl.
*C07C 17/38* (2006.01)
*B01D 53/22* (2006.01)
*B01D 53/70* (2006.01)
B01D 53/68 (2006.01)

(52) U.S. Cl.
CPC ........... *C07C 17/38* (2013.01); *B01D 53/226* (2013.01); *B01D 53/229* (2013.01); *B01D 53/228* (2013.01); *B01D 53/68* (2013.01); *B01D 53/70* (2013.01); *B01D 2053/224* (2013.01); *B01D 2251/306* (2013.01); *B01D 2251/604* (2013.01); *B01D 2256/26* (2013.01); *B01D 2257/102* (2013.01); *B01D 2257/104* (2013.01); *B01D 2257/2025* (2013.01); *B01D 2257/2045* (2013.01); *B01D 2257/2047* (2013.01); *B01D 2257/2064* (2013.01); *B01D 2257/2066* (2013.01); *B01D 2257/404* (2013.01); *B01D 2257/502* (2013.01); *B01D 2257/504* (2013.01); *B01D 2257/80* (2013.01); *Y02C 10/10* (2013.01); *Y02P 20/152* (2015.11); *Y02P 20/154* (2015.11)

(58) Field of Classification Search
CPC ...... C07C 17/38; B01D 53/22; B01D 53/228; Y02P 20/152; Y02P 20/154
See application file for complete search history.

(56) References Cited

U.S. PATENT DOCUMENTS

| | | |
|---|---|---|
| 5,196,616 A | 3/1993 | Lee et al. |
| 5,698,011 A | 12/1997 | Chung et al. |
| 6,156,097 A | 12/2000 | O'Brien et al. |
| 2003/0010618 A1 | 1/2003 | Clemmer |

FOREIGN PATENT DOCUMENTS

| | | |
|---|---|---|
| JP | H0459016 A | 2/1992 |
| WO | WO 2012/011609 A1 | 1/2012 |

*Primary Examiner* — Jafar Parsa
(74) *Attorney, Agent, or Firm* — Steven D. Boyd

(57) ABSTRACT

A method of separating a composition containing at least one organofluorine compound from at least one inorganic compound by contacts the composition with a semipermeable membrane. Other methods separate a organofluorine compound from a composition containing at least one other organofluorine compound or chlorocarbon. Methods also include isolating a single organofluorine compound from a composition comprising a mixture of organofluorine compounds, chlorocarbons, and/or inorganic compounds.

16 Claims, 6 Drawing Sheets

MeTHOD FOR SEPARATING
ORGANOFLUORINE COMPOUNDS USING
MEMBRANE

The present application claims priority to International Application serial number PCT/US2014/045644 filed Jul. 8, 2014, which claims priority to U.S. provisional application Ser. No. 61/845,405 filed Jul. 12, 2013 and U.S. provisional application Ser. No. 61/989,031 filed May 6, 2014.

FIELD OF THE INVENTION

This invention relates to the membrane separation of organofluorine compounds.

BACKGROUND OF THE INVENTION

Due to stricter regulations, there is a significant amount of research being conducted to identify and produce organofluorine compounds having a much lower global warming potential (GWP) and zero or near zero ozone depletion potential (ODP). For example, hydrofluoroolefins (HFOs) including HFO-1234yf (1,1,1,2-tetrafluoropropene), HFO-1234ze (1,1,1,3-tetrafluoropropene), and HFO-1243zf (1,1,1-trifluoropropene), and hydrochlorofluoroolefins (HCFOs) such as HCFO-1233zd (1,1,1-trifluoro-3-chloropropene) and HCFO-1233xf (1,1,1-trifluoro-2-chloropropene) have been identified as fluorocarbons having a lower GWP, and therefore are considered to be non-greenhouse gases. Additionally, the ODP of those compounds is zero or negligible. HFO-1234yf, HFO-1234ze, and HCFO-1233zd, which are environmentally acceptable, have also been found to have lower flammability, acceptable toxicity, and good performance. Therefore, these products are under consideration by the industry as refrigerants or refrigerant components of a blend, foam blowing agents, aerosol propellants, and solvents for metal degreasing.

However, the production of these and other organofluorine compounds often require substantial separation steps to isolate the compounds from other components present in the reaction product, including unreacted feedstock, undesirable byproducts, and coproducts.

Production of organofluorine compounds often results in the formation of other organofluorine compounds, organochlorines, and chlorofluorocarbons (collectively referred to herein as "coproducts of organofluorine production" or simply "coproducts"), as both intermediate products and coproducts that appear in the final reaction mixture. For example, production of HFO-1234yf often forms other coproducts, such as HCFC-244bb (2-chloro-1,1,1,2-tetrafluoropropane), HFC-245cb (1,1,1,2,2-pentafluoropropane), and HFO-1233xf. Production of HCFO-1233zd and HFO-1234ze often forms a reaction mixture comprising unsaturated coproducts, such as cis and trans HCFO-1232zd (c/t-2,3-dichloro-3,3-difluoropropene), cis and trans HCFO-1231zd (c/t-1,3,3-trichloro-2-fluoropropene), and HFO-1243zf, and saturated coproducts, such as HFC-245fa (1,1,1,3,3-pentafluoropropane), HCFC-244fa (3-chloro-1,1,1,3-tetrafluoropropane), HCFC-243fa (2,2-dichloro-1,1,1-trifluoropropane), HCFC-242fa (1,3,3-trichloro-1,1-difluoropropane), HCFC-241fa (1,1,3,3-tetrachloro-1-fluoropropane), and HCC-240fa (1,1,1,3,3-pentachloropropane). Many of these organofluorine compounds and coproducts of organofluorine production form azeotropes or azeotrope-like mixtures, which further complicates separation of the organofluorine compounds.

Undesirable components of the reaction product mixture may include unreacted hydrogen fluoride (HF), carbon monoxide (CO) and carbon dioxide ($CO_2$), water, and hydrogen chloride (HCl), oxygen, nitrogen, NOx, chlorine and impurities. Many of these organofluorine compounds are known to form an azeotrope or azeotrope-like mixtures with hydrogen fluoride, HF.

In conventional methods, the organofluorine compounds are separated from unreacted HF using separation techniques such as scrubbing, distillation, and phase separation.

In one conventional method, HF is removed from the organofluorine by water scrubbing, which is followed by organic drying and then distillation of the impure organic. The HF is discharged as waste aqueous HF.

In another conventional method, sulfuric acid is used to absorb HF from the organofluorine mixture. The HF is then desorbed, which allows the HF to be recycled back to the fluorination reactor. The use of sulfuric acid is limited because it can lead to unwanted reactions, such as the isomerization of trans-HCFO-1233zd to the toxic cis-HCFO-1233zd.

Other conventional methods include low temperature phase separation, in which an HF-rich phase is removed from an organic-rich phase. The HF-rich phase is then fed to a first azeotropic distillation column to recover the azeotrope as an overhead and pure HF as the bottoms. The organic-rich phase, which includes the organofluorine compound, such as HCFO-1233zd, is fed to a second distillation column to further separate HF from the organofluorine. For example, trans-HCFO-1233zd is removed from the top and cis-HCFO-1233zd is removed from the bottom along with HF.

Another conventional separation method comprises organic extractive distillation, which requires the addition of another solvent which is preferentially extracted with either the organofluorine component or HF. A second distillation is then used to recover the extractant from the organofluorine component or the HF.

Current processes for separating organofluorine compounds from other organofluorine compounds or coproducts of organofluorine production rely on distillation, most often azeotropic distillation. Distillation between certain organofluorine compounds and coproducts becomes increasingly difficult when the boiling points differ by 10° C. or less.

The conventional methods for separating organofluorine compounds are time-consuming and expensive, and, in many cases, involve the use of additional components, which require further separation to form an isolated product.

Membrane separation technology is widely used on many industrial processes such as, for example, gas permeation (e.g. separation of oxygen, nitrogen, helium from air; separation of hydrogen from hydrocarbon such as methane). Liquid separation membranes are used, for example, in the recovery of zinc from wastewater or nickel from electroplating solution. Reverse osmosis is used in desalination plants and in the treatment of waste water to remove impurities.

However, separation membranes have not been used in the fluorochemical industry, such as breaking an azotrope or azeotrope-like or separation of a organofluorine compound from another organofluorine compound, or separation of a organofluorine compound from an HF/organofluorine. A major issue with using membrane separations in the organofluorine industry is the absence of commercial separation membranes compatible with HF and organofluorine products.

Thus, there is a need for separation techniques for the recovery of organofluorine compounds that can be performed more quickly, less expensively, with less energy, and/or without the need for additional chemicals.

SUMMARY OF THE INVENTION

The present invention relates to a process for separating an organofluorine compound from a composition.

On aspect of the present invention relates to a process of separating at least one organofluorine compound from at least one inorganic compound. The process comprises contacting a composition comprising the at least one organofluorine compound and the at least one inorganic compound with at least one semipermeable membrane capable of selectively permeating the at least one inorganic compound to form a first stream rich in the at least one inorganic compound and a second stream rich in the at least one organofluorine compound.

Another aspect of the present invention relates to a process of separating a organofluorine compound from other organofluorine compounds or coproducts of organofluorine production. The process comprises contacting a composition comprising a organofluorine compound and at least one other organofluorine compound or coproduct of organofluorine production with at least one semipermeable membrane capable of selectively separating the organofluorine compound to form a first stream rich in the at least one organofluorine compound and a second stream rich in the at least one other organofluorine compound or coproduct of organofluorine production.

Yet another aspect of the present invention relates to a process of separating an organofluorine compound from a composition comprising at least one inorganic compound and at least one other organofluorine compound or coproduct of organofluorine production. The composition is contacted with at least one semipermeable membrane to separate the organofluorine compound from the at least one inorganic compound and the at least one other organofluorine compound or coproduct of organofluorine production

DETAILED DESCRIPTION OF THE INVENTION

Figure 1A:
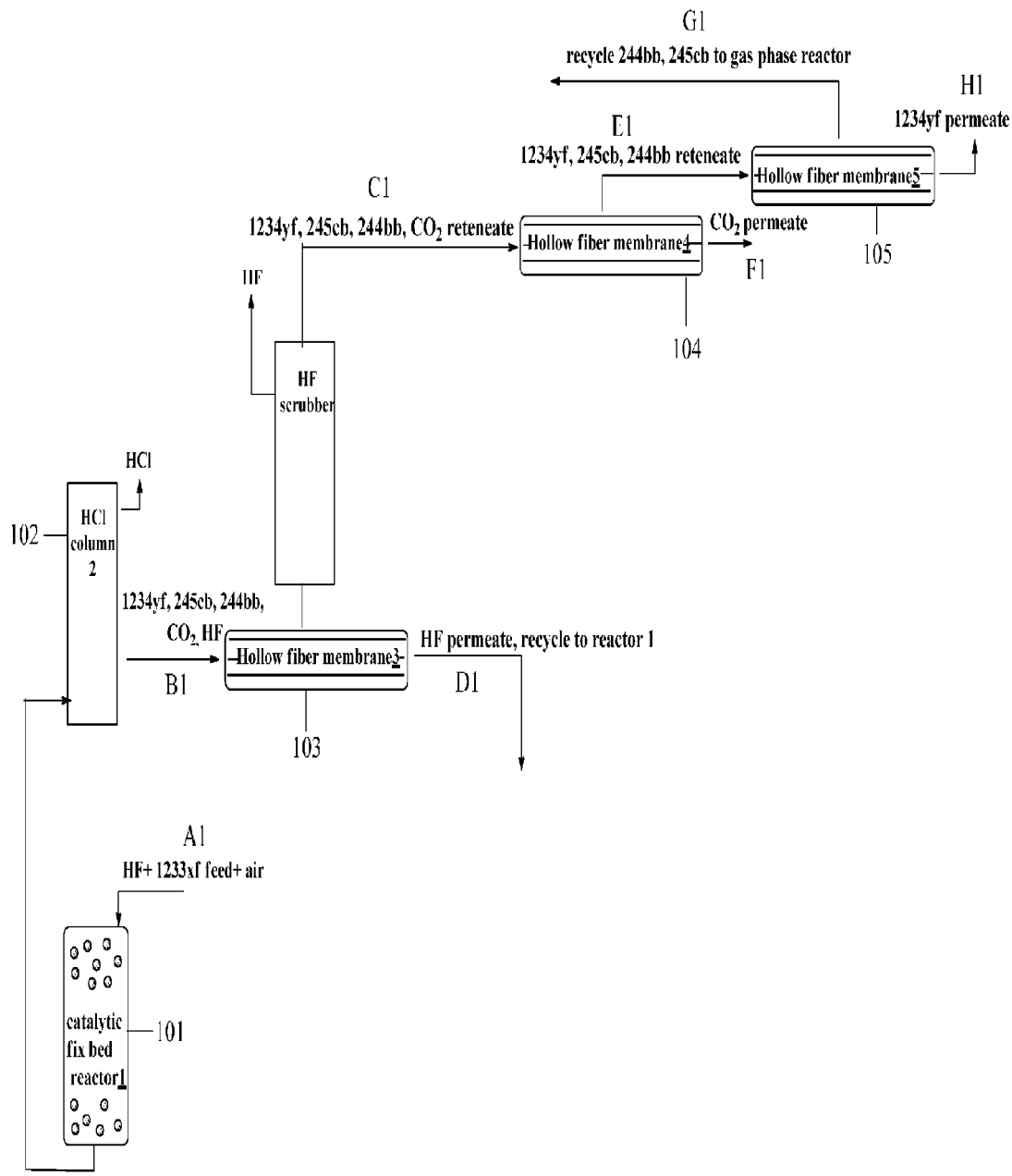
FIG. 1a shows a schematic flow diagram of a membrane separation process for the recovery of HFO-1234yf.

One aspect of the present invention relates to the membrane separation of at least one organofluorine compound from a composition comprising at least one organofluorine compound and at least one inorganic compound.

As used herein, the terms "organofluorine compound" or "organofluorine," refer to a compound comprising at least hydrogen, fluorine, and carbon. Organofluorine compounds that may be used in accordance with the present disclosure include, for example, hydrofluorocarbons (HFCs), hydrofluoroolefins (HFOs), hydrochlorofluorocarbons (HCFCs), and hydrochlorofluoroolefins (HCFOs). The term "organochlorine," as used herein, refers to compounds comprising at least hydrogen, chlorine, and carbon.

As used herein, the terms "coproducts of organofluorine production" and "coproducts" refer to organofluorine compounds produced in the reaction to form the desired organofluorine compound. For example, HCFC-245fa is among the coproducts that may be formed in the production of HCFO-1233zd and/or HFO-1234ze. The term "byproduct" is used herein to identify products of the organofluorine production process other than organofluorine compounds.

According to at least one embodiment, unreacted organic raw materials may also be removed from the desired organofluorine products. Unreacted organic raw materials may be separated, for example, by membrane separation, as described herein.

In accordance with at least one embodiment, the at least one organofluorine compound comprises at least 2 carbon atoms, at least 3 carbon atoms, at least 4 carbon atoms, or at least 5 carbon atoms. Examples of organofluorine compounds comprising 2 carbon atoms include HFC-134a and HFC-125. Examples of 3 carbon atom organofluorine compounds include hydrochlorofluoropropene and hydrofluoropropene. In at least one embodiment, the at least one organofluorine compound comprises at least 3 carbon atoms or at least 4 carbon atoms. In at least one embodiment, the at least one organofluorine compound comprises 3, 4, 5, or 6 carbon atoms. The at least one organofluorine compound may comprise a mixture of organofluorine compounds, such as mixtures of 3- and 4-carbon organofluorine compounds, mixtures of 5- and 6-carbon organofluorine compounds, and combinations of 3-, 4-, 5-, and 6-carbon organofluorine compounds.

Exemplary organofluorine compounds that may be used in accordance with at least one embodiment of the present disclosure include HFCs such as 23, 134a, 125, 32, 1132a, and 142b; HFOs such as 1234yf, 1234ze, 1243zf and 1336mzz; HCFOs such as 1233zd and 1233xf; and mixtures thereof. As one of ordinary skill in the art recognizes, this list of organofluorine compounds is not an exhaustive list and other organofluorines can be used in accordance with the embodiments of the present disclosure without departing from the scope of the invention.

As used herein, the term "inorganic compound" refers to compounds which do not comprise both carbon and hydrogen.

The at least one inorganic compound may include, for example, hydrogen fluoride (HF), carbon monoxide (CO), carbon dioxide ($CO_2$), hydrogen chloride (HCl), water, nitrogen, oxygen, NOx, chlorine and impurities. In at least one embodiment, the at least one inorganic compound comprises, consists of, or consists essentially of HF, CO, $CO_2$, HCl, and water. As used herein, the phrase "consists essentially of" excludes the presence of any other inorganic compound that would materially affect the separation of the at least one organofluorine compound from the at least one inorganic compound.

In at least one embodiment, the at least one inorganic compound comprises HF. The HF may be present in the form of hydrogen fluoride, e.g., hydrogen fluoride gas or liquid.

According to at least one embodiment, the composition may comprise other compounds, such as, for example, other reaction products resulting from the production of the organofluorine, such as byproducts and coproducts. In at least one embodiment, the separation process comprises separating the organofluorine compounds and any coproducts from the at least one inorganic compound and any byproducts of the organofluorine production process.

In at least one embodiment, the at least one inorganic compound and the at least one organofluorine compound form an azeotrope or an azeotrope-like mixture. As used herein, the term "azeotrope-like" means a mixture of at least two compounds that behave like azeotropic mixtures, which do not fractionate upon boiling or evaporation. Azeotrope and azeotrope-like mixtures are constant boiling and cannot be separated during a phase change from the liquid phase to the gas phase.

In at least one embodiment, the at least one inorganic compound comprises a polar compound. The polar compound may have a molecular weight of 100 Da or less, such as, for example, 75 daltons (Da) or less, 50 Da or less, 40 Da or less, or 30 Da or less.

The process in accordance with the present disclosure may comprise contacting the composition with at least one semipermeable membrane. As used herein, the term "semipermeable" means that the membrane is selectively permeable to one or more compounds such that it allows different gases, vapor or liquids to move through it at different rates. The membrane restricts the motion of molecules passing across it so that some molecules move more slowly than others or are excluded altogether (i.e., impermeable). For example, the membrane may be selectively permeable to the at least one inorganic compound and impermeable to the at least one organofluorine compound. The permeability of a membrane is dependent on its ability to partition different compounds and the diffusion of those compounds through the membrane. Separation membranes can selectively separate components over wide range of solubility parameters and molecular sizes, from macromolecular materials to simple ionic or covalent compounds. The key properties determining membrane performance are high selectivity and fluxes, good mechanical, chemical and thermal stability under operating conditions, low fouling tendencies and good compatibility with operating environment. The membrane separation process is characterized by the fact that a feed stream is divided into 2 streams: retentate and permeate.

The retentate is that part of the feed that does not pass through the membrane, while the permeate is that part of the feed that does pass through the membrane. An optional sweep is a gas or liquid that is used to help remove the permeate. The components of interest in the membrane separation is known as the solute. The solute can be retained on the membrane or passed through the membrane in the permeate.

There are three main mechanisms by which membrane can perform separations. In the first mechanism, size exclusion, the membrane has holes or pores of such a size that certain species can pass through and others cannot. In selective retardation or pore flow, the pore diameters are close to the molecular sizes of the compounds, slowing different compounds at different rates. The last mechanism, solution diffusion, occurs by dissolution of the compounds into the membrane, migration by molecular diffusion across the membrane, and reemergence from the other side. The separation process of the present invention may operate using one or more of these separation mechanisms.

In contrast with distillation processes, membrane separation does not require a phase separation, which generally provides a significant energy savings in comparison to distillation processes. Capital costs can also be reduced because membrane separation processes typically have no moving parts, no complex control schemes, and little ancillary equipment compared to other separation processes known in the art. Membranes can be produced with extremely high selectivity for the components to be separated. In general, the values of the selectivity are much higher than typical values for relative volatility for distillation operations. Membrane separation processes may also be able to recover minor but valuable components from main stream without substantial energy cost. Membrane separation processes are potentially better for the environment since the membrane approach require the use of relatively simple and non-harmful materials.

A wide range of mechanisms are available for separation using semipermeable membranes, such as, for example, size variability of the molecules, affinity for the membrane material, and permeation driving forces, such as concentration or pressure difference.

In at least one embodiment, the permeability of the membrane is characterized by a separation factor, $\alpha$, which is a measure of the preferential permeability of one compound or type of compound over another compound or type of compound. The separation factor is the ratio of the relative amount of a first compound that permeates the membrane to the relative amount of a second compound that permeates the membrane. Therefore, a separation factor of about 1 indicates that both compounds permeate the membrane in similar amounts. A separation factor greater than 1 indicates that one compound permeates the membrane in a greater amount than another compound.

In at least one embodiment, the separation factor, $\alpha$, is greater than about 1.5. The separation factor $$\alpha = \frac{[A]_{permeate}/[B]_{permeate}}{[A]_{retentate}/[B]_{retentate}}.$$

In at least one further embodiment, the separation factor, $\alpha$, is greater than about 2, such as greater than about 5, greater than about 10, greater than about 20, or greater than about 40. A higher separation factor, $\alpha$, indicates greater separation of compounds.

In at least one embodiment, the semipermeable membrane is selected such that the at least one inorganic compound selectively permeates the membrane in an amount greater than the at least one organofluorine compound. In alternative embodiments, the semipermeable membrane may be selected such that the at least one organofluorine compound permeates the membrane in an amount greater than the at least one inorganic compound.

The membrane may be operated at any temperature and/or pressure capable of separating the at least one organofluorine compound from the at least one inorganic compound.

For example, the separation process may be operated at a pressure ranging from about 1 psi to about 300 psi, such as from about 1 psi to about 100 psi. In at least one embodiment, the separation process is performed at a pressure of at least 1 psi, such as at least 2 psi, at least 5 psi, at least 10 psi, or at least 20 psi. According to at least one embodiment, the separation process is performed at a pressure of ranging from about 10 psi to about 50 psi.

The membrane performance can be driven by the pressure difference between the total feed pressure and the total permeate pressure. The pressure ratio of the feed pressure to permeate pressure may range from about 0.1 to about 50, such as, for example, from about 2 to about 30, or from about 5 to about 10.

In at least one embodiment, the separation process is carried out at a temperature ranging from about 0° C. to about 150° C., such as, for example, from about 0° C. to about 100° C., from about 10° C. to about 75° C., or from about 20° C. to about 50° C.

The membrane used in the embodiments of the present disclosure may be selected from any membrane in the art. For example, the membrane may comprise a film, a laminate, hollow fibers, coated fibers, etc. One of ordinary skill in the art will recognize that the selection of the appropriate membrane will depend on the selectivity of the membrane for the compounds being separated. The membrane may be provided on an inert support.

In at least one embodiment, the membrane comprises a polymer selected from polypropylene, polytetrafluoroethylene, polyvinylidene fluoride, polyvinyl fluoride, polychlorotrifluoroethylene, perfluoroalkoxy polymer, fluorinated ethylene-propylene, polyethylenetetrafluoroethylene, and perfluoropolyether. In at least one embodiment, the membrane is selected from polyvinylidene fluoride polymers, including polyvinylidene fluoride homopolymers and copolymers, such as the KYNAR® family of polyvinylidene fluoride polymers produced by Arkema Inc. Exemplary polyvinylidene fluoride polymers include, for example, KYNAR® HOMOPOLYMER, such as KYNAR® HOMOPOLYMER 460, 1000, 700, and 370, and KYNAR® COPOLYMER, such as, KYNAR® COPOLYMER 2500, 2750/2950, 2800/2900, 2850, and 3120 series.

In at least one embodiment, the membrane comprises a polymer selected from polyimide membranes, such as those commercially available from Ciba Geigy under the trade name MATRIMID® 5218 polyimides. Polyimide membranes may be preferably used for selectively permeating $CO_2$ gas from saturated or unsaturated organofluorine compounds.

In at least one embodiment, the composition comprises a mixture of at least one organofluorine compound and HF. HF is known to be highly corrosive and rapidly degrades many polymers. Therefore, the membrane for separating the HF from the organofluorine compounds may be selected from membranes that are stable in the presence of HF, such as fluorinated polymers including polyvinylidene fluoride polymers.

In accordance with at least one embodiment, the membrane is selectively permeable to HF, i.e., the separation factor, α, is greater than 1 for the permeability of HF with respect to the at least one organofluorine compound. Separation by the semipermeable membrane results in a HF-rich first stream, i.e., a permeate stream and a organofluorine-rich second stream, i.e., a retentate stream.

In accordance with at least one embodiment of the present disclosure, the resulting first stream and/or second stream may be subjected to an additional separation process, such as, for example, an adsorption process, a distillation process, a phase separation process, or an additional membrane separation process. For example, the first stream, such as the HF-rich permeate stream described above, may be subjected to a further separation process to isolate the HF. Similarly, the residual stream may be subjected to a further separation process to further purify the at least one organofluorine compound.

In the above example, the membrane is permeable to HF and impermeable to the organofluorine compound. In accordance with the present disclosure, the membrane can be permeable or impermeable to the organofluorine compound. For example, the membrane may have a separation factor, α, greater than 1 or less than 1. A membrane may separate the components based on size, solubility, or other selection criteria.

The process according to the present disclosure may provide a clean enough stream of organofluorine to require minimal clean up prior to the product being used in the final desired application.

Another aspect of the present invention relates to separation of a organofluorine compound from a composition comprising other organofluorine compounds or coproducts of organofluorine production. For example, a organofluorine production process may produce the desired organofluorine compound or target organofluorine, as well as coproducts including other organofluorines.

In at least one embodiment, the composition comprises a mixture of at least one organofluorine compound, such as HFO-1234yf, HFO-1234ze, HFO-1243zf, HCFO-1233zd, and HCFO-1233xf, from saturated or unsaturated organofluorine compounds and organochlorines. These organofluorine compound products are known to be corrosive and rapidly degrades many polymeric material. Therefore, the membrane for separating a organofluorine compound from organofluorine products may be selected from membranes that are compatible with these organofluorines such as fluorinated polymers including polyvinylidene fluorides and polyimides.

In accordance with at least one embodiment, the membrane is selectively permeable to the desired organofluorine compound, i.e., the separation factor, α, is greater than 1 for the permeability of the desired organofluorine compound with respect to the other organofluorines. Separation by the semipermeable membrane results in a desired organofluorine-rich first stream, i.e., a permeate stream, and a second stream, i.e., a residual stream, rich in the other organofluorine compounds.

In at least one embodiment, the composition may comprise a mixture of saturated organofluorine compounds and organochlorines (e.g., HFCs, HCFCs, and HCCs) and unsaturated organofluorines (e.g., HFOs, HCFOs). According to at least one embodiment, the membrane may selectively separate the unsaturated organofluorine compounds from the saturated organofluorine compounds. The process may result in a HFO and/or HCFO rich first stream and a second stream rich in saturated organofluorine compounds.

In accordance with at least one embodiment of the present disclosure, the resulting first stream and/or second stream may be subjected to an additional separation process, such as, for example, an adsorption process, a distillation process, a phase separation process, or another membrane separation process. For example, the first stream, such as the HFO and/or HCFO-rich permeate stream described above, may be subjected to a further separation process to isolate the HFO and/or HCFO. Similarly, the residual stream may be subjected to a further separation process to further purify the saturated organofluorine compounds and chlorocarbons.

In the above example, the membrane is permeable to HFO and HCFO and impermeable to the other organofluorine compounds and chlorocarbons. In accordance with the present disclosure, the membrane can be permeable or impermeable to the HFOs/HCFOs or other targeted group or compound. For example, the membrane may have a separation factor, α, greater than 1 or less than 1. A membrane may separate the components based on molecular size, solubility, or other selection criteria.

In accordance with at least one embodiment, the composition may comprise a plurality of saturated and unsaturated organofluorine compounds. One or membranes may be selected to separate a single desired organofluorine compound from the composition.

The process according to the present disclosure may provide a clean enough stream of organofluorine compound to require minimal clean up prior to the product being used in the final desired application.

Another aspect of the present invention relates to the separation of a organofluorine compound from a composition comprising other organofluorine compounds, as well as inorganic compounds or other byproducts. The composition may be subjected to one or more membrane separations to isolate the organofluorine compound from the other compounds in the composition.

In at least one embodiment, the composition may comprise a mixture of HFOs and/or HCFCs and $CO_2$, which may be subjected to a membrane separation process to separate the HFOs and/or HCFOs from the $CO_2$.

One known processes for the production of HFO-1234yf is based on the catalytic gas phase fluorination of HCFO-1233xf, as shown in Scheme 1:

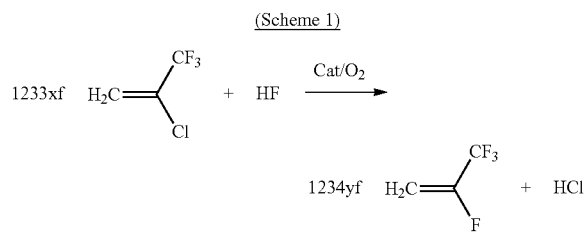

In order to maintain the catalyst active for extended period of time, the process requires the co-feed of high levels of oxygen, in the form of air. The oxygen co-feed reacts downstream to form $CO_2$, resulting from burning coke deposit on the catalyst. The composition exiting the reaction includes the organic products, as well as unreacted HF, produced HCl and $CO_2$. In conventional water scrubbing processes, both HF and HCl are lost as aqueous HCl and aqueous HF, in addition to some useful organic products lost as soluble organic in water that are difficult to be recover.

Figure 1B:
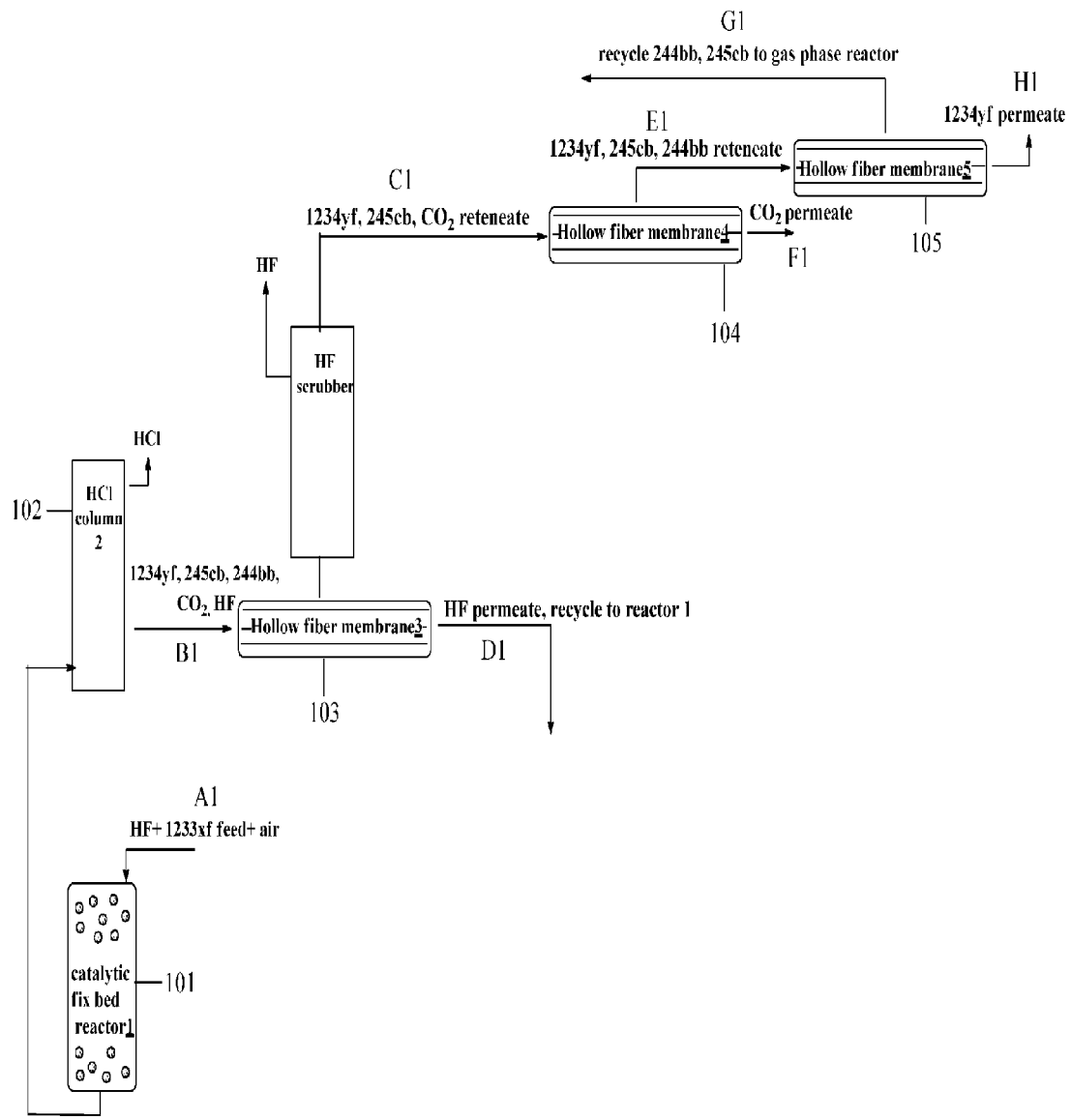
FIG. 1b shows a schematic flow diagram of an alternate membrane separation process for the recovery of HFO-1234yf.

According to an embodiment of the present disclosure, membranes can be used to recover HF, HFO-1234yf, and $CO_2$ as relatively pure permeate streams from the composition, without loss of HF or the desired product, as shown in FIG. 1.

In the catalytic gas phase fluorination of HCFO-1233xf to HFO-1234yf and/or HFC-245cb, the feed A1 comprising HCFO-1233xf, together with HF and air, is admitted to the gas phase reactor 101, containing the catalyst of choice and is attached to the HCl distillation column 102. The HCl collected from the top of the column 102, is water scrubbed or purified and used for other applications. Heavies B1, such as HFO-1234yf, HFC-245cb, HCFC-244bb, $CO_2$ and HCl, are collected from the bottom of column 102 and passed over hollow fiber membrane 103. Any other type of membrane fabrication known in the art can also be used. The polymeric membrane is composed of polyvinylidene fluoride. The membrane is capable of permeating HF in a permeate stream D1, which can be recycled back to the gas phase reactor 101.

The retained HFO-1234yf, HFC-245cb, HCFC-244bb, and $CO_2$ in retentate C1 is then allowed to pass over another hollow fiber membrane 104, composed of the commercial grad MATRIMID® 5218 polyimide (available from Ciba Geigy) which can form permeate F1 comprising $CO_2$ and form retentate E1 comprising HFO-1234yf, HFC-245cb, and HCFC-244bb. This retained organic product is then passed over another hollow fiber membrane 105, composed of a KYNAR® membrane 2801, known as MILLIPORE PVDF, which was found to be sufficient to permeate HFO-1234yf and retain HCFC-244bb and HFC-245cb, forming permeate H1 and retentate G1, respectively. This retained HCFC-244bb and HFC-245cb can be recycle back to the primary gas phase reactor 101.

HCFO-1233zd can be manufactured using feed stock such as HCC-240fa, HCO-1230za or HCO-1230xf. The reaction scheme for forming HCFO-1233zd from HCC-240fa is shown in Scheme 2:

(Scheme 2)

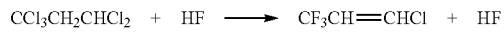

In conventional processes, the recovery of HCFO-1233zd requires some combination of low temperature induced phase separation, water scrubbing of HF, or azeotropic distillation to recover organic form HF. This conventional process can consume large amounts of energy or in the case of aqueous scrubbing, wastes large amounts of HF.

Figure 2:
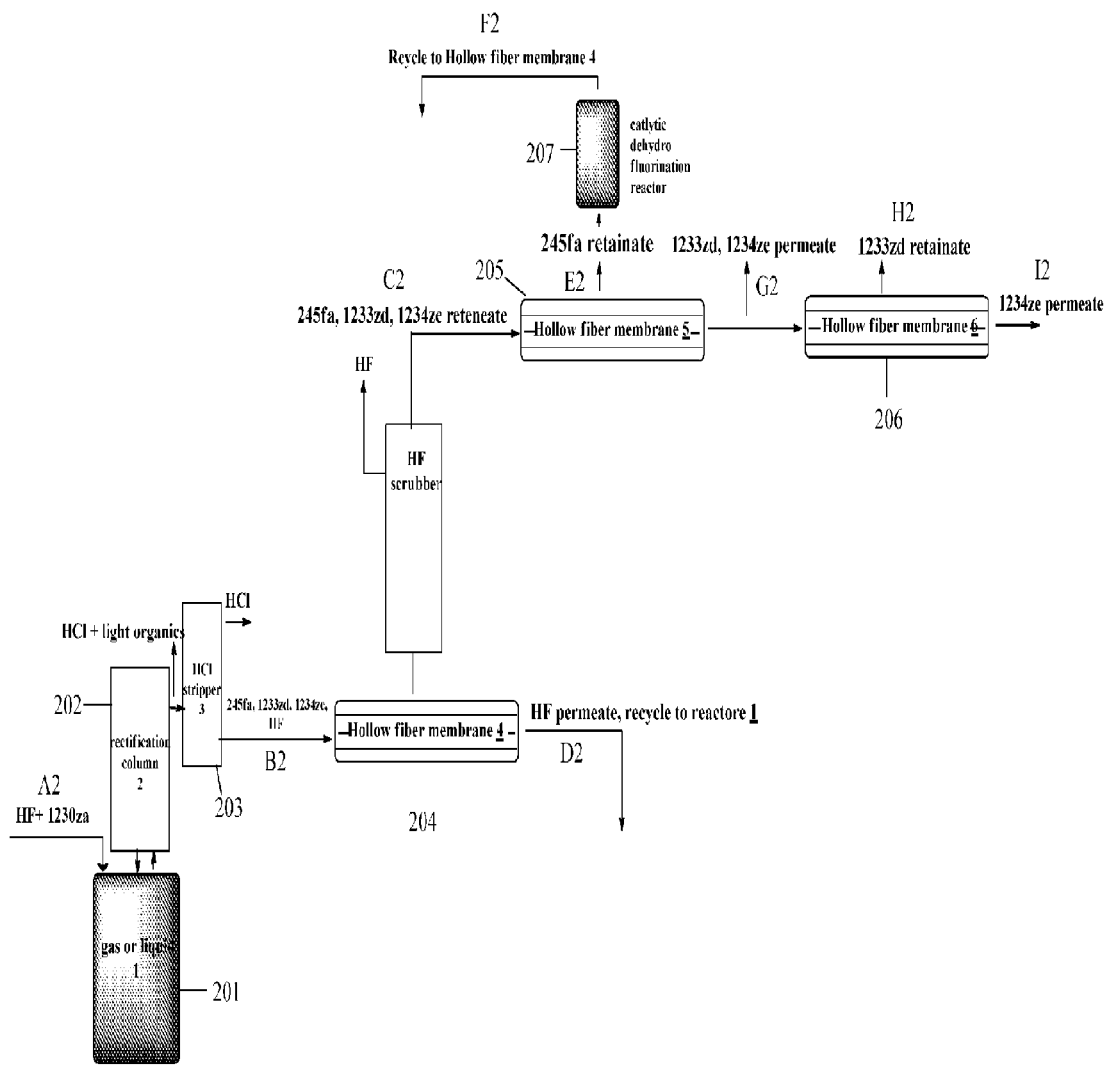
FIG. 2 shows a schematic flow diagram of a membrane separation process for the recovery of HCFO-1233zd and HFO-1234ze.

According to an embodiment of the present disclosure, membrane separation is used to recover the products and HF. A process for the recovery of HCFO-1233zd is shown schematically in FIG. 2. In FIG. 2, the feed A2 comprising HCO-1230za, together with HF as a fluorinating agent, is admitted to the liquid phase reactor 201.

The reaction products containing anhydrous liquid HF can be fed into a rectification column 202. The operating temperature and pressure can be adjusted in such a way to maintain heavy organics, HCO-1230za, HCFO-1231zd, HCFO-1232zd, and HF in the reactor 1. Meanwhile, volatile products and coproducts such as HCFO-1233zd, HFO-1234ze, HFC-245fa, HCl, and HF can be removed from the top of the column 202 and admitted to the HCl stripper column 203. The HCl collected from the top of the column 202, can be water scrubbed or purified and used for other applications.

Heavies B2 such as HCFO-HCFO-1233zd, HFO-1234ze, HFC-245fa, and HF, can be collected from the bottom of the HCl column 203 and passed over hollow fiber membrane 204. Other types of membranes which are known in the art can also be used. The polymeric membrane can be composed of poly vinylidene fluoride (PVDF). The membrane 204 is capable of permeating HF and retaining the organic HCFO-1233zd, HFO-1234ze, and HFC-245fa to form permeate D2 and retentate C2, respectively.

The permeated HF (D2) can be recycled back to the liquid phase reactor 201. Meanwhile, the retained organofluorine compound stream (C2) can be passed over another hollow fiber membrane 205, composed of membrane material suited for permeating HCFO-1233zd and HFO-1234ze and retaining HFC-245fa, such as the PVDF KYNAR® sold as MILLIPORE KYNAR® 2801. Other membranes sufficient to separate HFC-245fa from the two olefins HCFO-1233zd and HFO-1234yf can also be used.

The retentate E2 comprising HFC-245fa can be dehydrofluorinated using a separate gas phase reactor to produce HFO-1234ze, as shown in Scheme 3

(Scheme 3)

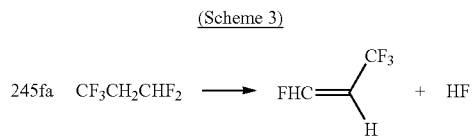

The resulting product mixture F2 comprising HFO-1234ze, HF, together with unreacted HFC-245fa, can be recycled back to the membrane 204, for the recovery of HF and organofluorine compound product HFO-1234ze and unreacted HFC-245fa. The permeate G2 comprising the HCFO-1233zd and HFO-1234ze from membrane 205, can be separated using hollow fiber membrane 206, composed of the KYNAR® GELMAN FP-200, or other membrane which is sufficient to separate HCFO-1233zd from HFO-1234ze and form permeate 12 and retentate H2, respectively.

Because there is a large range of boiling points between the two isomers of permeated c/t-HFO-1234ze (the cis isomer has a boiling point of 5° C. and the boiling point of the trans isomer is −19° C.), the two isomers can be separated by simple distillation. Similarly, the large difference in boiling point between c/t-HCFO-1233zd (cis isomer boils at 40° C. and the trans isomer boils at 18° C.) allows the isomers to be separated by simple distillation.

In at least one embodiment, the separation membrane may comprise a fluoropolymer in the main backbone of the polymer chain and a highly acidic —SO$_3$H group adjacent to a difluoromethylene group in the side chain, such as in NAFION® MEMBRANE (Formula 1).

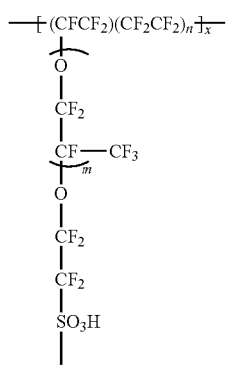

(Formula 1)

In the method described above, the separated HCFO-1233zd can be isomerizatized to trans-HCFO-1233zd by passing the HCFO-1233zd over a NAFION® membrane, to form equilibrium mixture of c/t-HCFO-1233zd. The proportion of the isomers, depends on the operating conditions. For example, a thermodynamic equilibrium mixture will be produced if the operating conditions correspond to equilibrium conditions. However, if the operating conditions are the kinetic conditions, then the kinetically favorable isomer will be the predominant isomer. Therefore, by operating under kinetically favorable conditions, the trans isomer can be produced in greater abundance, as shown in Scheme 4.

(Scheme 4)

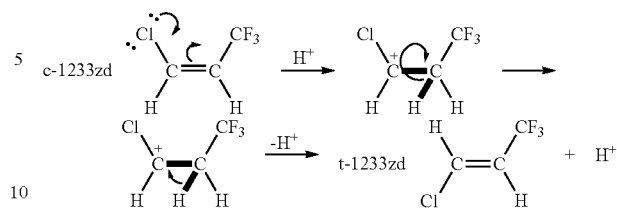

The following examples illustrate the present invention without limiting the scope thereof.

EXAMPLES

Examples 1-6

Evaluation of Polymer Membrane for Chemical and Mechanical Stability

Experiments were carried out in triplicate as follow. Polymeric film approximately 1×1×¼ inch was placed in a 500 cc, stainless steel Parr reactor, which was leak tested with helium at 100 psig for approximately 30 minutes. Approximately 50 grams of anhydrous liquid HF was condensed into liquid nitrogen precooled Parr reactor, followed by another 50 grams of HFC-134a. Subsequently, the reactor was placed in a thermostated water bath, at 20° C. for two weeks. After venting the organofluorine compound and HF, the polymeric film was washed with plenty of water and was tested for any discoloration, weight loss or mechanical disintegration. An average of triplicate runs is reported in Table 1.

TABLE 1

Chemical and mechanical stability of membrane material, in the presence of 50/50 weight % mixture of HF and HFC-134a (CF$_3$CH$_2$F), tested at 20° C. for two weeks.

| Example | Membrane material | Observation | Recommendation |
|---|---|---|---|
| 1 | CELGUARD® POLYPROPYLENE | White color lost Intact | Candidate |
| 2 | Polyvinyl chloride | Brown Intact | Not recommended |
| 3 | Polyethylene LD | Brown Brittle | Not recommended |
| 4 | Polyethylene HD | Slight yellow Intact | Not recommended |
| 5 | KYNAR® blend | Slight discoloration Intact | Candidate |
| 6 | KYNAR® 2801 PVDF_9µm | Clear colorless Intact | Good candidate |

Examples 7-15

Evaluation of Supported and Unsupported Polymeric Membrane for the Separation of 50/50 Weight % HF/HFC-134a Blend A supported membrane such as KYNAR® 2801 PVDF on a Millipore 0.1 µm support was prepared as follows. 3 weight % solution of KYNAR® 2801 PVDF in acetone was sprayed onto a 142 mm diameter Millipore support. Several coats were applied to cover the entire support surface evenly. Typical membrane thicknesses of 0.8 to 5 µm were obtained.

Leaks greater than one bubble every ten seconds were rejected for membrane testing.

The polymeric materials were cut into 47 mm discs (membrane) and placed in a modified Millipore SS filter holder (test cell) with stainless steel screens and TEFLON® O-rings. The test cells had Swagelok inlet and outlet ports on each side for the feed, rejectate and permeate flows. The test cell was placed in a constant temperature bath maintained at 20±1° C.

HF and 134a gases were fed from two separate stainless steel 316 lines. The flow rate of the two gases were measured and controlled using a mass flow controller. The two gases were mixed together and were fed into a micrometering valve which controlled the transmembrane operating pressure. The gases flowed through a 4-way valve which directed the feed and permeate flows either to a gas chromatograph (GC) or to the aqueous potassium hydroxide (KOH) scrubber. The test gas was passed across the feed side of the membrane which was placed in a constant temperature (i.e., ±1° C.) air thermostated oven. The permeate side of the test cell was swept with a constant flow of helium gas at a rate of 8-10 cc/min, which carried out the permeating gases to the GC for analysis. The outlet lines from the test cell were connected to GOW-MAC gas chromatograph equipped with a thermal conductivity detector and a 0.5 cc sample loop to perform periodic sampling. The effluent gases from the GC, were vented to a KOH scrubber solution. The permeate gases were analyzed at 60 minute intervals. An integrator was used to calculate area % for every component including HF. This process was repeated at 0.1, 2.5 and 5 psig operating pressure. Results obtained are summarized in Table 2. A separation factor α equal to one or near one, indicates that there is no preferential separation of HF over 134a. A separation factor greater than one indicates that there is preferential separation of HF over 134a. A separation factor less than one indicates preferential separation of 134a over HF.

TABLE 2

Separation performance of various composite membrane

| Material Mem/support | Transmembrane Pressure psi | T ° C. | Alpha α HF/134a |
|---|---|---|---|
| 7. EYPEL ®-F/GELMAN | 2.5 | 32 | .66 |
| 8. PVDF/GELMAN | 2.5 | 55 | 2.68 |
| 9. EYPEL ®-F/ZITEX ® | 2.5 | 32 | 1.01 |
| 10. PVDF/KYNAR ® | 2.5 | 55 | 1.81 |
| 11. Eypel ®-F/ZITEX ® | 5 | 32 | .96 |
| 12. PVDF 2801/Millipore | 5 | 55 | 58.2 |
| 13. PVDF 2801/Millipore | 2 | 55 | 15.8 |
| 14. PVDF 2801/Millipore | .1 | 32 | 3.5 |
| 15. PVDF 2801/Millipore | .1 | 55 | 6.9 |

The data summarized in Table 2, suggested that the membrane made out of KYNAR® 2801 PVDF supported on Millipore is selectively permeating HF from a HF and 134a mixture.

Examples 16-27

Effect of Temperature on a Composite Membrane (KYNAR® 2801 PVDF Spray Coated on a Millipore Support)

The PVDF 2801-Millipore composite membrane was the most efficient membrane in separating HF from 134a mixture. In addition, it was stable in a HF environment for over 120 hours. Therefore, it can be used to recover HF and recycle it back to the gas phase reactor without additional purification. This membrane was further tested for the measurement of flux and durability of the membrane. The result obtained is shown in Table 3.

TABLE 3

Separation performance of KYNAR® 2801 PVDF supported on a Millipore support at 5 psi

| Example | HF/134a | Feed % | Permeate HF/134a | Flux $g/m^2 \cdot hr$ HF/134a | T ° C. | A HF/134a |
|---|---|---|---|---|---|---|
| 16 | 10/1 | 91/1 | 94.4/5.6 | 14630/870 | 30 | 1.66 |
| 17 | 10/1 | 91/1 | 81.3/18.7 | 24380/5596 | 50 | .43 |
| 18 | 3/1 | 75/25 | 96.7/3.3 | 21381/723 | 30 | 9.85 |
| 19 | 3/1 | 75/25 | 94.5/5.5 | 14711/860 | 50 | 5.7 |
| 20 | 1/1 | 50/50 | 97.6/2.4 | 14629/361 | 30 | 40.55 |
| 21 | 1/1 | 50/50 | 97.8/2.2 | 17256/378 | 50 | 45.59 |
| 22 | 1/4 | 20/80 | 91.3/8.7 | 10209/973 | 30 | 41.98 |
| 23 | 1/4 | 20/80 | 91.1/8.9 | 6300/616 | 50 | 40.92 |
| 24 | 1/16 | 5.88/94.12 | 75.1/24.9 | 2154/716 | 30 | 48.18 |
| 25 | 1/16 | 5.88/94.12 | 74.4/25.6 | 2342/805 | 50 | 46.55 |
| 26 | 1/64 | 1.5/98.5 | 20.7/79.3 | 206/791 | 30 | 17.11 |
| 27 | 1/64 | 1.5/98.5 | 25.0/75.0 | 363/1088 | 50 | 21.92 |

*Membrane thickness 0.00032 cm, surface area 132.73 $cm^2$

Example 28

Separation of a HF/HFC-134a Azeotrope Mixture, Using KYNAR® 2801 PVDF Supported on a Millipore Support An azeotropic homogeneous mixture of HF/HFC-134a 15 g·mol/85 g·mol is placed in gas cylinder, which is electrically heated at 40° C. The gas mixture is passed over the above membrane, at a feed rate of 100 cc/min, using a mass flow meter controller.

The permeate is absorbed in a standard solution of 0.1 M KOH. After continuous feed for 16 hours, the remaining KOH scrubber solution indicates neutralization of 0.64 moles by the acid present in the permeate. Analysis of rejectate feed is expected to indicate no acid present, suggesting that this membrane is selective for permeating HF but not HFC 134a.

Example 29

Separation of HF/HCFO-1233zd Azeotrope Mixture, Using KYNAR® 2801 PVDF Supported on a Millipore Support An azeotropic mixture composed of HF and HCFO-1233zd is prepared by mixing 290 g of HF and 100 g of 1233zd. The azeotropic mixture is placed in gas cylinder and is heated electrically. A steady state flow of 100 cc/min is fed over the membrane, which is kept at 20° C., at an operating pressure of 5 psi using a pressure transducer. The gaseous permeate is scrubbed using a standard solution of 0.1 M KOH. After 10 hours of continues feed of the gas mixture through the membrane, quantitative analysis of the KOH solution is predicted to indicate that the entire HF equivalent in the feed is neutralized with the KOH solution. The rejectate is expected to only contain HFCO-1233zd.

Example 30

Separation of a HF/HCFO-1234yf Azeotrope Mixture, Using a KYNAR® 2801 PVDF on a Millipore Support An azeotropic mixture composed of HF and HCFO-1234yf is prepared by mixing 51.4 g of HF and 861.9 g of 1234yf. The azeotropic mixture is placed in gas cylinder and is heated up electrically. A steady state flow 100 cc/min is fed over the above membrane, which is kept at 20° C., at an operating pressure of 5 psi using a pressure transducer. The gaseous permeate is scrubbed using a standard solution of 0.1 M KOH. After 18 hours of continuous feed of the gas mixture through the membrane, quantitative analysis of the KOH solution is predicted to indicate that all of the HF equivalent in the feed is neutralized with the KOH solution. The rejectate is expected to only contain HCFO-1234yf.

Example 31

Separation of HF/HCFO-1233xf Azeotrope Mixture Using KYNAR® 2801 PVDF on a Millipore Support An azeotropic mixture composed of 25.4 g of HF and 1162.84 g of HCFO-1233xf is mixed together and placed in gas cylinder and heated to 25° C. Steady state flow of 100 cc/min is fed over the above membrane at 25° C. and at an operating pressure of 35.2 psi using a pressure transducer. The gaseous permeate is scrubbed using a standard solution of 0.1M KOH solution. After 21 hours of continuous feed, analysis of the rejectate indicates no HF present in the organofluorine. Analysis of the KOH solution is predicted to indicate that there is 56 ml of 0.1 M KOH consumed, suggesting that all of the HF in the permeate is neutralized, providing evidence that the above membrane is selective in permeating HF and none of the organofluorine compound.

Example 32

Figure 3:
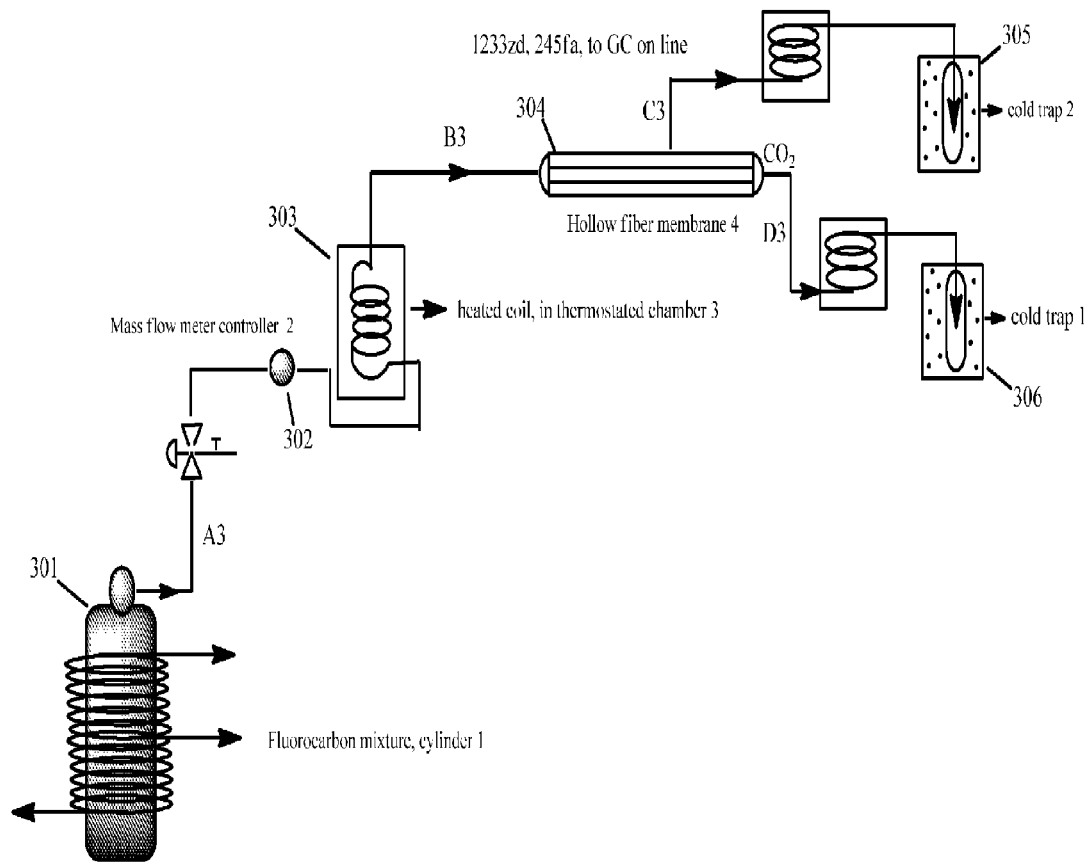
FIG. 3 shows a schematic flow diagram of a membrane separation process for the separation of $CO_2$ from a mixture containing HCFO-1233zd, HFO-1234ze, and HFC-245fa.

Membrane Separation of $CO_2$ from a Mixture Containing HCFO-1233zd, HFO-1234Ze and HFC-245Fa A schematic flowchart of the membrane separation of $CO_2$ from a mixture containing HCFO-1233zd, HFO-1234ze and HFC-245fa is shown in FIG. 3. A mixture composed of HFC-245fa (2 grams, 0.0149 mol), HCFO-1233zd (1.1 grams, 0.0084 mol), HFO-1234ze (0.9 grams, 0.0079 mol), and $CO_2$ (2.1 grams, 0.0477 mol) is mixed together and placed in a pressure cylinder 301 and was heated up using electrical coil, as shown in FIG. 3. The gas mixture A3 is fed at a flow rate of 20 ccm (cubic centimeter per minute), using gas mass flow meter 302 and then to heating coil 303 placed in thermostated water bath. After leaving the coil, the gases B3 enter the inlet side of a separation membrane 304 comprised of a polyimide membrane in the form of 360 hollow fibers 73 cm long having outside diameter of 160 µm and pore diameter of 90 µm. The membrane 304 is composed of MATRIMID® 5218 (Ciba Geigy) polyimide skin covering a bulk porous wall made of ULTEM® 1000 (General Electric). The permeated gas D3 comprising $CO_2$ is collected in a cold trap 306 using liquid nitrogen. Analysis of the gas stream, using inline gas chromatography (GC) shows no organic collected accumulated on cold trap 306. After 3.5 hours at a 20 ccm flow rate, the total amount of $CO_2$ collected in the cold trap 306 is 4.99 grams, which is equivalent to the calculated value using mass flow meter (e.g., 20 ccm×60 min×3.5 hours=4200 cc total flow, and 4200×60.4%=2537 cc of $CO_2$=0.1135 mol=4.99 g of $CO_2$).

TABLE 4

| Feed composition of organofluorine compound and $CO_2$ | |
|---|---|
| Organofluorine, $CO_2$ feed Composition | Total cubic centimeter cc, % cc |
| 245fa 2.0 g, .015 m | 334, 18.9% |
| 1233zd 1.1 g, .008 m | 189, 10.7% |
| 1234ze 0.9 g, .008 m | 177, 10.0% |
| $CO_2$ 2.1 g, .048 m | 1070, 60.4% |

In this example no attempt is made to separate the retained organofluorine gases C3.

Example 33

Figure 4:
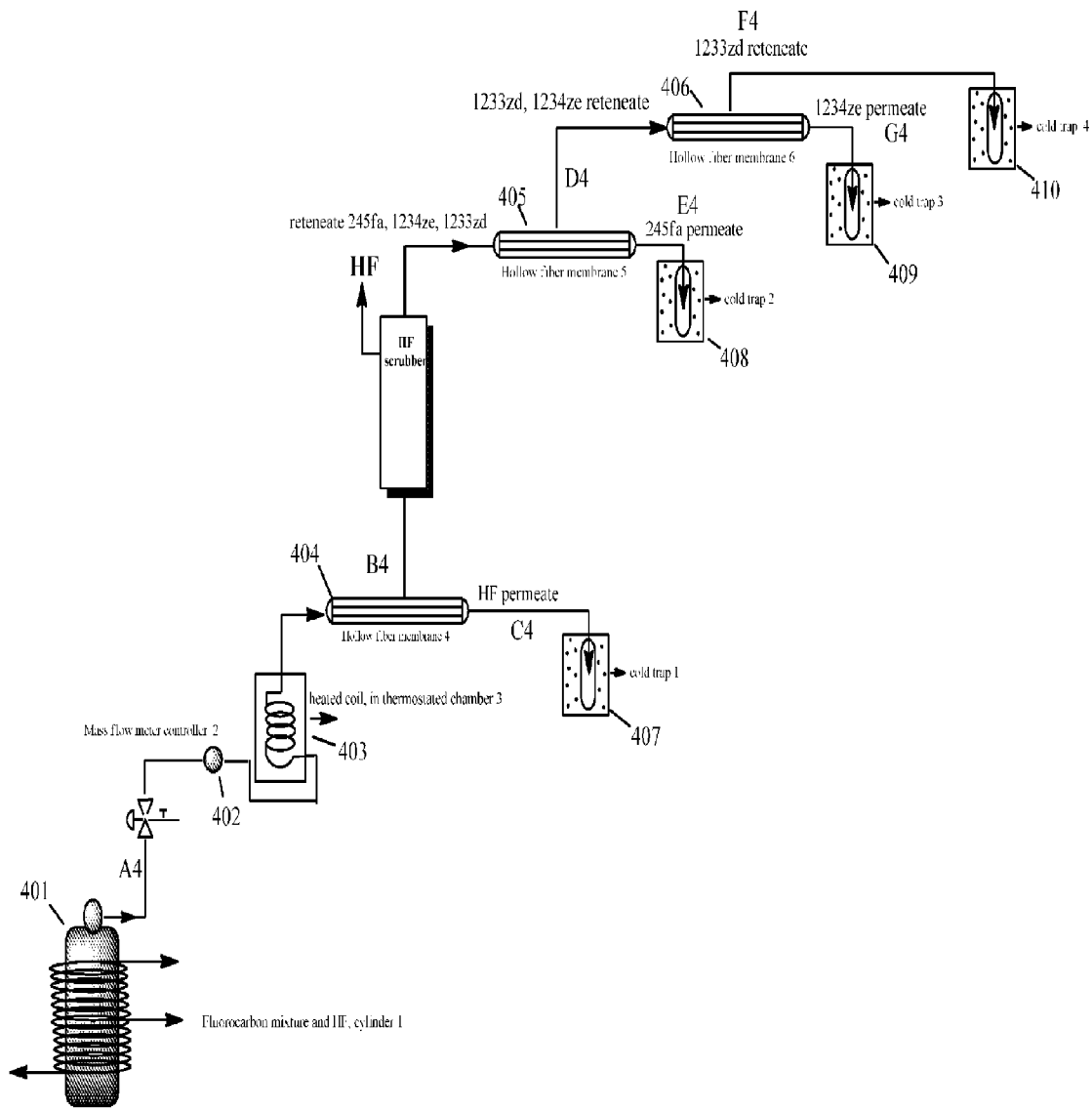
FIG. 4 shows a schematic flow diagram of a membrane separation process for the recovery of HF, HFC-245fa, HCFO-1233zd, and HFO-1234ze.

Separation of HCFO-1233zd from a Mixture Containing HF, HCFO-1233zd, HFC-245Fa, and HFO-1234Ze A schematic diagram showing the separation of HCFO-1233zd from a mixture containing HF, HCFO-1233zd, HFC- 245fa, and HFO-1234ze is shown in FIG. 4. A organofluorine mixture composed of HCFO-1233zd (38.56 g, 0.295 mol), HFC-245fa (2.25 g, 0.0168 mol), HFO-1234ze (1.5 g, 0.00877 mol) was mixed together with HF (5.6 g, 0.28 mol) and placed in cylinder 401, which was heated up electrically, as shown in FIG. 4. A steady flow of 25 ccm of gas mixture A4 was fed and controlled by mass flow meter controller 402 into heated and thermostated coil 403 to ensure all the organofluorine components and HF were in the gas phase. The feed mixture was admitted to the separation membrane 404, which was composed of KYNAR® 2801, 0.1 μm Millipore PVDF membrane, prefabricated as a hollow fiber membrane. The permeate C4 containing HF was collected in the cold trap 407. The retentate B4 containing the organofluorines HFC-245fa, HFO-1234ze and HCFO-1233zd was admitted to another separation membrane 405 comprised of KYNAR® 2801 PVDF 0.2 μm membrane, commercially available from Arkema Inc.

The permeate E4 from membrane 405 containing HFC-245fa was collected using cold trap 408 while the retentate D4 containing HCFO-1233zd and HFO-1234yf was passed through separation membrane 406 comprised of Millipore KYNAR® 2801 PVDF 0.3 μm membrane.

The permeate G4 from membrane 406 was collected in the cold trap 409 and was identified as HCFO-1234ze, and the retentate F4 containing organofluorine gas was collected in cold trap 410 and identified as HCFO-1233zd. All chemical analyses of the organofluorine were carried out using gas chromatography, comparing retention time of an authentic sample and the retention time of the organofluorine under investigation.

After feeding for 2.5 hours, using feed rate of 25 ccm, the amount of HF collected in the cold trap 407 was determined to be 0.484 g. The calculated value from the above feed rate 25 ccm×60×2.5 hr×0.14478/1000×22.41×20=0.484 g. There was good agreement between the found HF collected and calculated organofluorine mixture and HF.

TABLE 5

Summary of the results obtained for separation of HCFO-1233zd from a mixture containing HF, HCFO-1233zd, HFC-245fa, and HFO-1234ze.

| Trap | Found[1] (g) | Calculated[2] (g) |
|---|---|---|
| 407 - HF | 0.484 | .484 |
| 408 - HFC-245fa | 0.3766 | .3765 |
| 409 - HFO-1234ze | 0.25 | .24 |
| 410 - HCFO-1233zd | 16.9 | 16.9 |

[1]Collected in cold trap
[2][Feed rate ccm × 60 × Hours of feed × (volume component % in feed/1000) × 22.414] × molecular weight = weight in grams Example 34

Separation of $CO_2$, HF, HCFO-1233zd, HFO-1234Ze, and HFC-245Fa

Figure 5:
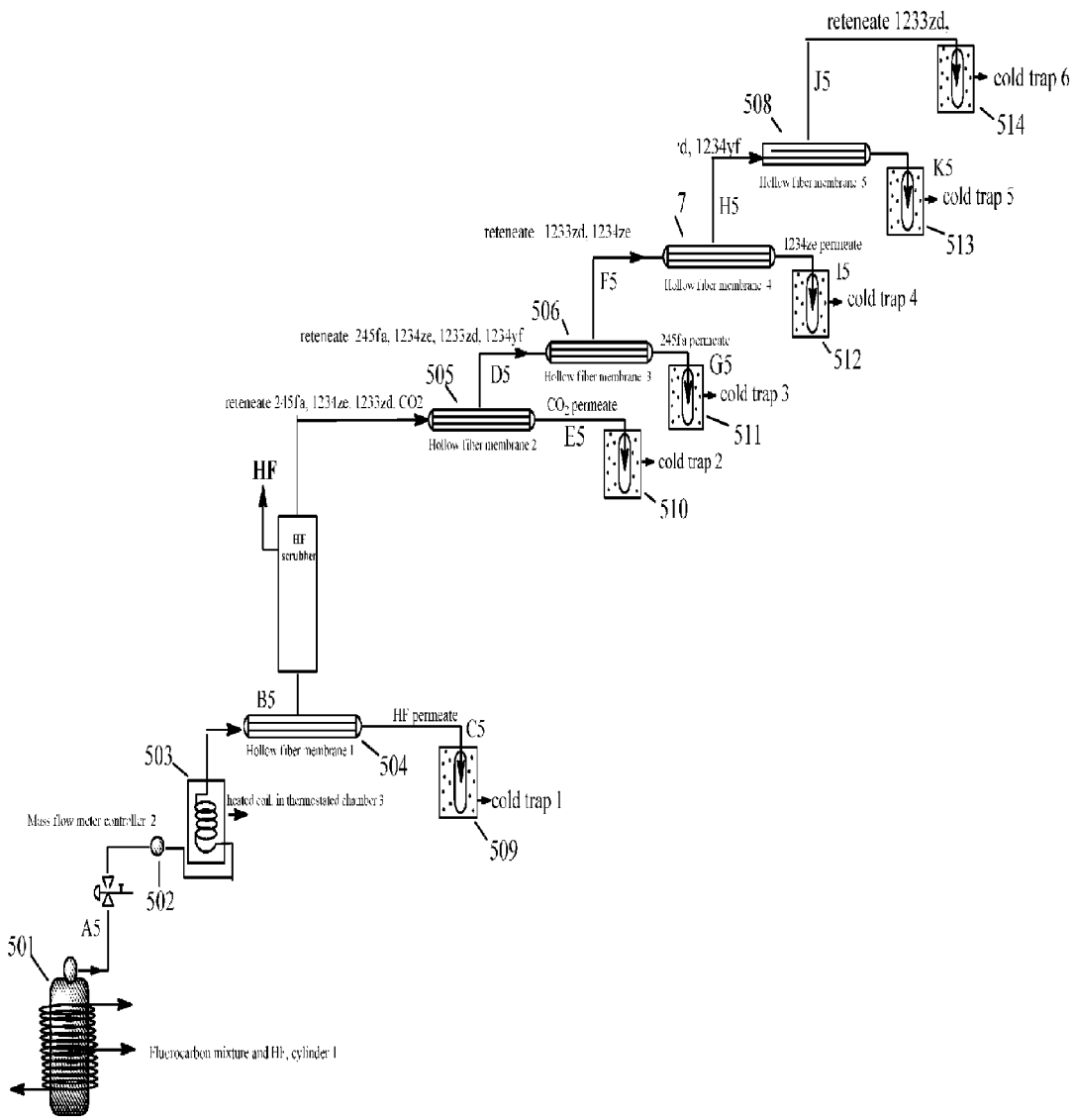
FIG. 5 shows a schematic flow diagram of a membrane separation process for the recovery of HF, HFC-245fa, HFO-1234ze, and HCFO-1233zd.

A schematic diagram showing the separation of $CO_2$, HF, HCFO-1233zd, HFO-1234ze, and HFC-245fa is shown in FIG. 5. A organofluorine compound mixture composed of HF (2.5 g, 0.125 mol), $CO_2$ (0.15 g, 0.0034 mol), HFC-245fa (0.26 g, 0.0019 mol), HFO-1234ze (4.3 g, 0.0363 mol), and HCFO-1233zd (5.2 g, 0.0398 mol) is placed in cylinder 501 and is heated up electrically, as shown in FIG. 5. A steady flow of 30.5 ccm of the gas mixture A5 is fed, using mass flow meter controller 502, into heated and thermostated coil 503, to ensure all components in the mixture are in the gas phase. The feed mixture is admitted to a separation membrane 504, which is composed of polyvinylidene fluoride (PVDF) 0.1 μm Millipore PVDF membrane, prefabricated as a hollow fiber separation membrane. The permeate C5 containing HF gas is collected in a cold trap 509.

The retained organofluorine stream B5 comprised of HFC-245fa, HCFO-1233zd, and HFO-1234ze, together with the $CO_2$ gas, enters the inlet side of a separation membrane 505, backed with commercial polyimide membrane in the form of 360 hollow fibers 73 cm long having outside diameter of 160 μm and pore diameter of 90 μm. The separation membrane 505 comprises a MATRIMID® 5218 polyimide skin (Ciba Geigy) covering a bulk porous wall made of ULTEM® 1000 (General Electric). The permeate E5 from membrane 505 containing $CO_2$ gas is collected in a cold trap 510.

The retained gas mixture D5 from membrane 505 containing HFC-245fa, HFO-1234ze, and HCFO-1233zd, is passed over a hollow fiber separation membrane 506 comprised of KYNAR® 2801 PVDF 0.2 μm membrane, commercially available from Arkema Inc. The permeate G5 contains HFC-245fa and is collected using cold trap 511.

The retentate F5 of separation membrane 506 containing HFO-1234ze, and HCFO-1233zd, enters a separation membrane 507, composed of KYNAR® PVDF 0.3 μm membrane. The permeated organofluorine I5 is collected in cold trap 512 and is identified by gas chromatography as HFO-1234ze.

The retained organofluorine compound gas H5 composed of HCFO-1233zd is collected in a cold trap 513 and is chemically identified as HCFO-1233zd.

After feeding for 2.5 hours, the weight of individual component, is calculated based on the above feed rate and compared to the actual amounts found in the cold traps. The results are summarized in Table 6.

TABLE 6

Summary of collected organofluorines, HF, and $CO_2$ collected in cold traps compared to calculated value from the gas mixture feed.

| Trap | Found[1] (g) | Calculated[2] (g) |
|---|---|---|
| 509 - HF | 2.18 | 2.180 |
| 510 - $CO_2$ | 0.131 | 0.131 |
| 511 - HFC-245fa | 0.226 | 0.226 |
| 512 - HFO-1234ze | 3.662 | 3.662 |
| 513 - HCFO-1233zd | 4.536 | 4.536 |

[1]Collected from the cold trap
[2][Feed rate ccm × 60 × 2.5 × (individual component percentage/1000) × 22.414] molecular weight.

Example 35

Bi-Functional Membrane for Organofluorine Separation and Isomerization Processes In this example, c/t-HFO-1234ze was separated and isomerized in a process using a separation membrane comprising NAFION®. c/t-HFO-1234ze was separated from the coproducts such as HFC-245fa, HCFC-244fa, and HCFC-243fa, as well as HCF, and the cis-1234ze was isomerized to the trans-1234ze.

We claim:
1. A process for separating an organofluorine compound from a composition, comprising:

contacting a feed stream comprising at least one first unsaturated organofluorine compound selected from the group consisting of HFO-1234yf, HFO-1234ze, HFO-1243zf, HCRO-1233zd, HCFO-1233xf and mixtures thereof, and at least one additional compound selected from the group consisting of saturated organofluorine compounds, second unsaturated organofluorine compounds, organochlorines, inorganic compounds and mixtures thereof with a semipermeable membrane comprising at least on polymer selected from the group consisting of polypropylene, polytetrafluoroethylene, polyvinylidene fluoride, polyvinyl fluoride, polychlorotrifluoroethylene, perfluoroalkoxy polymer, fluorinated ethylene-propylene, polyethylenetetrafluoroethylene, and perfluoropolyether to form a first stream rich in the at least one first unsaturated organofluorine compound.

2. The process of claim 1, wherein the feed stream comprises at least one first unsaturated organofluorine compound and at least one inorganic compound, and contacting the feed stream with said semipermeable membrane forms a first stream rich in the at least one first unsaturated organofluorine compound and a second stream rich in the at least one inorganic compound.

3. The process of claim 2, wherein the at least one first unsaturated organofluorine compound and the at least one inorganic compound form an azeotrope or azeotrope-like mixture.

4. The process of claim 2, wherein the at least one inorganic compound is selected from the group consisting of hydrogen fluoride (HF), carbon monoxide (CO), carbon dioxide ($CO_2$), hydrogen chloride (HCl), water, oxygen, nitrogen, NOx, chlorine, and mixtures thereof.

5. The process of claim 4, wherein the at least one inorganic compound comprises HF.

6. The process of claim 1, wherein the feed stream comprises a first unsaturated organofluorine compound and at least one additional organofluorine compound and/or chlorocarbon, and contacting the feed stream with said semipermeable membrane forms a first stream rich in the first unsaturated organofluorine compound and a second stream rich in the at least one additional organofluorine compound and/or organochlorine.

7. The process of claim 6, further comprising subjecting the second stream to at an additional separation process selected from the group consistiong of an adsorption process, a distillation process, a phase separation process, an additional membrane separation process and combinations thereof.

8. The process of claim 1, wherein the feed stream comprises a first unsaturated organofluorine compound, at least one additional organofluorine compound and/or organochlorine, and at least one inorganic compound, wherein contacting the feed stream with said semipermeable membrane forms a first stream rich in the first unsaturated organofluorine compound and the at least one additional organofluorine compound and/or organochlorine and a second stream rich in the at least one inorganic compound.

9. The process of claim 8, further comprising contacting the first stream with a second semipermeable membrane to form a first stream rich in the first unsaturated organofluorine compound and a second stream rich in the at least one additional organofluorine compound and/or organochlorine.

10. The process of claim 8, further comprising separating the first unsaturated organotluorine compound and each of the at least one additional organofluorine compound and/or chlorocarbon into individual streams by contacting the first stream rich in the first unsaturated organofluorine compound and the at least one additional organofluorine compound and/or organochlorine with a series of additional semipermeable membranes.

11. The process of claim 1, wherein the at least one inorganic compound comprises a polar compound having a molecular weight of 50 Da or less.

12. The process of claim 1, wherein the at least one unsaturated organofluorine compound comprises 3 to 6 carbon atoms.

13. The process of claim 1, wherein the semipermeable membrane is selected from the group consisting of a film, a laminate structure, hollow fibers, and coated fibers.

14. The process of claim 1, wherein the semipermeable membrane comprises polyvinylidene fluoride.

15. The process of claim 1, wherein the process is carried out at a temperature ranging from about 0° C. to about 150° C.

16. The process of claim 1, further comprising subjecting the first stream to an additional separation process selected from the group consisting of an adsorption process, a distillation process, a phase separation process, an additional membrane separation process and combinations thereof.

* * * * *